United States Patent
Friese

Patent Number: 5,681,784
Date of Patent: Oct. 28, 1997

[54] THERMAL SHOCK RESISTANT CERAMIC

[75] Inventor: Karl-Hermann Friese, Leonberg, Germany

[73] Assignee: Robert Bosch GmbH, Stuttgart, Germany

[21] Appl. No.: 542,969

[22] Filed: Oct. 13, 1995

Related U.S. Application Data

[63] Continuation-in-part of Ser. No. 162,193, filed as PCT/DE93/00524, Jun. 6, 1993, published as WO94/01762, Jun. 20, 1994, abandoned.

[30] Foreign Application Priority Data

Jul. 3, 1992 [DE] Germany .......................... 42 21 786.5

[51] Int. Cl.$^6$ .................................................. C04B 35/48
[52] U.S. Cl. .......................... 501/103; 501/105; 501/153; 252/520; 252/521; 204/421; 204/424; 204/425; 204/427; 429/33; 429/193
[58] Field of Search ..................................... 501/103, 105, 501/152, 153; 428/389, 404; 423/69, 71, 76; 429/193, 33; 204/421, 424, 425, 426, 427, 429; 252/507, 508, 509, 520, 521

[56] References Cited

U.S. PATENT DOCUMENTS

| | | | |
|---|---|---|---|
| 4,221,650 | 9/1980 | Friese et al. | 501/105 |
| 4,525,464 | 6/1985 | Claussen et al. | |
| 4,900,492 | 2/1990 | Claussen et al. | |
| 5,130,210 | 7/1992 | Iwasaki et al. | 501/105 |
| 5,296,421 | 3/1994 | Nishida et al. | 501/105 |
| 5,326,519 | 7/1994 | Claussen | 501/105 |

FOREIGN PATENT DOCUMENTS

| | | |
|---|---|---|
| 0209081A2 | 1/1987 | European Pat. Off. . |
| 0414575A1 | 2/1991 | European Pat. Off. . |
| 0454138A2 | 10/1991 | European Pat. Off. . |
| 2810134 | 9/1979 | Germany . |
| 3345659 A1 | 12/1984 | Germany . |
| 3415803 A1 | 10/1985 | Germany . |
| 63282124 | 3/1989 | Japan . |
| 1051377 | 6/1989 | Japan . |
| 2204030 | 11/1988 | United Kingdom . |
| 92/12105 | 7/1992 | WIPO . |

*Primary Examiner*—Paul Marcantoni
*Attorney, Agent, or Firm*—Spencer & Frank

[57] ABSTRACT

A ceramic which is thermal shock resistant and which is a sintered, homogeneous mixture of first and second ceramic powders, including a first ceramic powder which is based on at least one tetravalent oxide selected from the group including zirconium dioxide, hafnium dioxide, and thorium dioxide, and which is further composed of at least one stabilizer oxide selected from the group including oxides effective to stabilize the at least one tetravalent oxide; and a second ceramic powder which is based on at least one tetravalent oxide selected from the group including zirconium dioxide, hafnium dioxide, and thorium dioxide, which contains from 0 to 2.5 mole % of at least one stabilizer oxide based on that molar amount of $Y_2O_3$, and which has grains whose surface is at least partly covered by a coating effective to inhibit diffusion of cations from the at least one stabilizer oxide during sintering, and wherein the first ceramic powder has a higher stabilizer content than that of the second ceramic powder.

16 Claims, 1 Drawing Sheet

THERMAL SHOCK RESISTANT CERAMIC

CROSS-REFERENCE TO RELATED APPLICATION

This application is a Continuation-in-Part of application Ser. No. 08/162,193 filed as PCT/DE93/00524, Jun. 6, 1993 published as WO94/01762, Jun. 20, 1994 (now abandoned).

BACKGROUND OF THE INVENTION

1. Field of the Invention

The invention relates to a temperature-resistant ceramic. Such materials are of industrial importance, in particular as ion-conducting shaped bodies which can, for example, be platelet- or finger-shaped, on their mutually opposite surfaces have electrodes and optionally protective layers and can be used as measuring sensors for exhaust gases, for example, of motor vehicles. Essential demands placed on the ceramic solid electrolyte in this application concern the mechanical properties, such as strength and thermal-shock resistance, and also the electrical properties, in particular the ion conductivity.

2. Description of the Related Art

One way of simultaneously improving the mechanical properties and the $O^{2-}$-ion conductivity is, according to DE-P 41 00 105.2 which is not a prior publication, to use at least two commercial ceramic powders having different stabilizer-oxide contents for producing a ceramic solid electrolyte, thus exploiting the good mechanical properties of the ceramic with the low stabilizer content and at the same time the good conductivity properties of the ceramic with the high content.

Good mechanical properties and simultaneously good $O^{2-}$-ion conductivity are also obtained, according to EP-A 209 081, by cosintering at least one powder having a sufficiently high stabilizer-oxide content to form cubic zirconium dioxide in the final product, with at least one powder having a lower stabilizer-oxide content which is to be present in the tetragonal modification in the final product. In this process the highly-stabilized, i.e., high-stabilizer, powder preferably contains 8% by weight of yttrium oxide, compared with 4% by weight of yttrium oxide for the powder with a low stabilizer content.

It is known from DE-A 38 13 731 to coat zirconium dioxide particles with water-containing oxides in a wet treatment process. For this purpose, an aqueous dispersion of the particulate zirconium dioxide is treated with water-soluble salts which, on hydrolysis, form the water-containing oxides of the coating. By raising the pH, the water-containing oxide coating is deposited and the product is subsequently separated off by filtration, washed, dried and optionally milled. The product, due to it having the oxide additives as a coating, exhibits good dispersion and intimate mixing of the zirconium dioxide with the oxide additives.

For the technically/commercially important use for producing lambda sensors for the determination of oxygen partial pressure in exhaust gases of combustion engines, the known ceramic solid electrolyte materials have a still unsatisfactory resistance under the extreme conditions in the exhaust gas unit of motor vehicles, in particular, not yet fully satisfactory resistance to impact, cyclic fatigue and thermal shock.

A solid electrolyte-ceramic of fully stable zirconium dioxide is known from U.S. Pat. No. 5,130,210 to Iwasaki et al. In order to increase the mechanical stability of a solid electrolyte-ceramic, a metal oxide powder, for example, $Al_2O_3$, with an average grain size of 3 to 20 μm is added to the fully stabilized zirconium dioxide as a grain growth inhibitor. The metal oxide powder has a grain size which is considerably smaller than the grain size of the fully stabilized zirconium dioxide powder. The metal oxide powder attaches itself to the surface of the zirconium dioxide grains and thus inhibits the grain growth of the zirconium dioxide grains during the sintering of the powder so that the mechanical strength of the ceramic is increased.

An improvement of the thermal shock resistance, as is necessary, for example, in solid electrolyte-ceramics for gas sensors which are employed in exhaust gas producing equipment with large temperature changes, is not possible with the solid electrolyte-ceramic of Iwasaki et al. Moreover, since the fully stabilized zirconium oxide of the solid electrolyte-ceramic employed should bestow a sufficiently high ionic conductivity, the individual fully-stabilized zirconium dioxide grain must not be too strongly wetted with, i.e., coated by, the fine metal oxide powder. In no case, however, may a complete surrounding of the fully stabilized zirconium dioxide grains take place. In such cases, the electrical or ionic conductivity of the fully-stabilized zirconium dioxide grains is destroyed or so strongly influenced that no useful ionic conductivity of the solid electrolyte-ceramic exists.

SUMMARY OF THE INVENTION

Compared therewith, the ceramic of the invention has the advantage of having increased mechanical resistance to impact, cyclic fatigue and, in particular, also thermal shock.

The invention provides a ceramic which is thermal shock resistant and which is a sintered, homogeneous mixture of first and second ceramic powders, comprising a first ceramic powder which is comprised of at least one tetravalent oxide selected from the group consisting of zirconium dioxide, hafnium dioxide, and thorium dioxide, and at least one stabilizer oxide selected from the group consisting of oxides effective to stabilize the at least one tetravalent oxide and thereby provide a stabilized oxide after sintering; and a second ceramic powder which is comprised of at least one tetravalent oxide selected from the group consisting of zirconium dioxide, hafnium dioxide, and thorium dioxide, and from 0 to 2.5 mole % of at least one stabilizer oxide, and which is at least partly covered by a coating comprised of an oxide material present in an amount (a) which is effective to inhibit diffusion of cations from the at least one stabilizer oxide of the first ceramic powder into the second ceramic powder and (b) which is effective to inhibit uncontrolled grain growth, wherein the first ceramic powder has a higher stabilizer oxide content than that of the second ceramic powder, and wherein only the second ceramic powder is covered by a said coating, and wherein the coating on the grains of the second granular ceramic material comprises at least one oxide material selected from the group consisting of $Al_2O_3$, $Ga_2O_3$, and $Na$-$\beta$-$Al_2O_3$.

The second ceramic powder advantageously comprises at least on one stabilizer oxide, and the at least one stabilizer oxide of the second ceramic powder advantageously includes $Y_2O_3$. The first ceramic powder advantageously has a content of the at least one stabilizer oxide of at least 4 mole %. The first ceramic powder advantageously has a grain size which ranges from 0.5 to 2 μm, and the second ceramic powder advantageously has a grain size which is less than 0.5 μm.

The first ceramic powder may be prepared by coprecipitation of a suspension containing the at least one tetravalent oxide and the at least one stabilizer oxide to provide a coprecipitate, calcination of the coprecipitate, and subsequent milling.

The first ceramic powder and the second ceramic powder are advantageously present in a weight ratio which ranges from 75:25 to 95:5, preferably, 90:10.

The at least one tetravalent oxide of the second ceramic powder advantageously comprises a mixture of $ZrO_2$, and the oxide material advantageously is $Al_2O_3$. The second ceramic powder advantageously comprises 10% by weight of $Al_2O_3$.

The first ceramic powder advantageously comprises $ZrO_2$, and the at least one stabilizer oxide content advantageously ranges from 4 to 10 mole % of $Y_2O_3$.

The first ceramic powder may be prepared by melting a mixture containing the at least one tetravalent oxide and the at least one stabilizer oxide in an electric arc to provide a melt, cooling the melt to provide a mass, and milling the mass to provide grains having a grain size which ranges from 1 to 2 µm.

The ceramic may advantageously be a ceramic solid electrolyte suitable for use in a gas sensor.

The invention additionally provides a ceramic which is thermal shock resistant, which has a good oxygen ion conductivity effective for use of the ceramic in a measuring sensor of exhaust gases, and which is a sintered, homogeneous mixture of first and second ceramic powders, comprising a first granular ceramic material which is comprised of at least one tetravalent oxide selected from the group consisting of zirconium dioxide, hafnium dioxide, and thorium dioxide, and at least one stabilizer oxide selected from the group consisting of oxides effective to stabilize the at least one tetravalent oxide and thereby provide a fully stabilized oxide having good oxygen ion conductivity; and a second granular ceramic material which is comprised of at least one tetravalent oxide selected from the group consisting of zirconium dioxide, hafnium dioxide, and thorium dioxide, and at least one stabilizer oxide in an amount which ranges up to 2.5 mole %, and in which the grains thereof are substantially covered by a coating comprised of an oxide material present in an amount (a) which is effective to inhibit diffusion of cations from the at least one stabilizer oxide in the first ceramic powder into the second ceramic powder and (b) which is effective to inhibit uncontrolled grain growth, wherein the first ceramic powder has a higher stabilizer oxide content than that of the second ceramic powder, wherein only the second granular ceramic powder material is covered by a said coating, and wherein the coating on the grains of the second granular ceramic material comprises at least one oxide material selected from the group consisting of $Al_2O_3$, $Ga_2O_3$, and Na-$\beta$-$Al_2O_3$.

The first granular ceramic material advantageously has a grain size which ranges from 0.5 to 2 µm, and the second granular ceramic material advantageously has a grain size which is less than 0.5 µm. The first granular ceramic material and the second granular ceramic material are advantageously present in a weight ratio which ranges from 75:25 to 95:5.

The first granular ceramic material and the second granular ceramic material advantageously comprise $ZrO_2$, the at least one stabilizer oxide contained in the first granular ceramic material and in the second granular ceramic material advantageously is $Y_2O_3$, and the $Y_2O_3$ in the first granular ceramic material is advantageously present in an amount ranging from 4 to 10 mole %.

The ceramic of the invention is preferably a solid electrolyte; in this case, in addition to improving the mechanical properties, use of the microstructure-straining second ceramic powder coated with diffusion-inhibiting oxides gives the advantage that the $O^{2-}$-ion conductivity of the first, highly-stabilized ceramic powder is not impaired.

However, the invention can likewise be applied to temperature-resistant ceramics which are not solid electrolytes, for example, mullite, cordierite, glass ceramic, zirconium silicate, and others.

It is known to improve the strength of $ZrO_2$ ceramic by introducing tetragonal $ZrO_2$ particles into a matrix of highly stabilized cubic $ZrO_2$; on cooling after the sintering process, these tetragonal particles transform into the monoclinic phase with an increase in the lattice volume and thereby produce a straining of the microstructure and thus an increase in the strength of the ceramic, (see for example, R. Stevens: *Zirconia and Zirconia Ceramics*, Magnesium Elektron Ltd., 1986, pages 17, 18). It has furthermore been known to further increase the stressing of the microstructure and, hence the strength of the $ZrO_2$ ceramic, by addition of $Al_2O_3$.

Compared therewith, the invention achieves considerable technical advantages, in particular improved strength, fracture toughness and thermal-shock resistance, by coating at least one ceramic powder which has a low stabilizer content or is unstabilized with an oxide which inhibits diffusion of the stabilizer-oxide cations and subsequently, in a known manner, mixing this powder with at least one highly-stabilized ceramic powder, pressing and subsequently sintering. It is particularly advantageous to use for this purpose a low stabilizer content or unstabilized $ZrO_2$ having a coating of $Al_2O_3$. A similar effect is also achieved with $Ga_2O_3$ or Na-$\beta$-$Al_2O_3$ alone, in admixture with one another or in admixture with $Al_2O_3$. The oxide coating on the ceramic powders which have a low stabilizer content or are unstabilized inhibits an equalization of the stabilizer-oxide concentrations between highly stabilized ceramic grains and ceramic grains which have a low stabilizer content or are unstabilized during the sintering process and makes possible a homogeneous distribution of the highly stabilized regions having good $O^{2-}$-ion conductivity and also the regions which have a low stabilizer content or are unstabilized and which lead to the increase in strength by phase transformation. In a particularly advantageous manner, the oxide coating inhibits uncontrolled grain growth during the sintering process. By the advantageous use of fine ceramic powder, in particular of highly stabilized ceramic powder having a particle size from about 0.5 to 2 µm and ceramic powder which has a low stabilizer content or is unstabilized and has a particle size below 0.5 µm, very fine-grained microstructures can thus be achieved in the sintered ceramic.

The generally known stabilizer oxides may be used as the stabilizer component of the stabilized zirconium dioxide of the present invention. These are known, for example, from Vielstich's book, *Fuel Cells*, Wiley Interscience (English translation copyrighted 1970), pps. 248–261, and the articles referred to therein, and the work of Strickler and Carlson reported in part in *J. Am. Ceramic Soc.*, Vol. 48, pps. 286–289 (June, 1965), and the so-called yttrium concentrate containing oxides of rare earth elements (A. K. Kuznetsow et al. in *Refractories*, No. 6, pps. 393–395 (1971)), etc. Preferred stabilizer oxides include, but are not limited to, $Y_2O_3$, $Yb_2O_3$, CaO or mixtures thereof, or mixtures of CaO and MgO.

It is possible to prepare the first, highly stabilized ceramic powder in a conventional manner by coprecipitation of $O^{2-}$-conducting oxides and stabilizer oxides. However, both the first and also the second ceramic powder can be particularly advantageously obtained by coating of $ZrO_2$ in a wet-treatment process, as described, for example, in DE-A 38 13 731.

DESCRIPTION OF THE PREFERRED EMBODIMENTS

Figure 1:
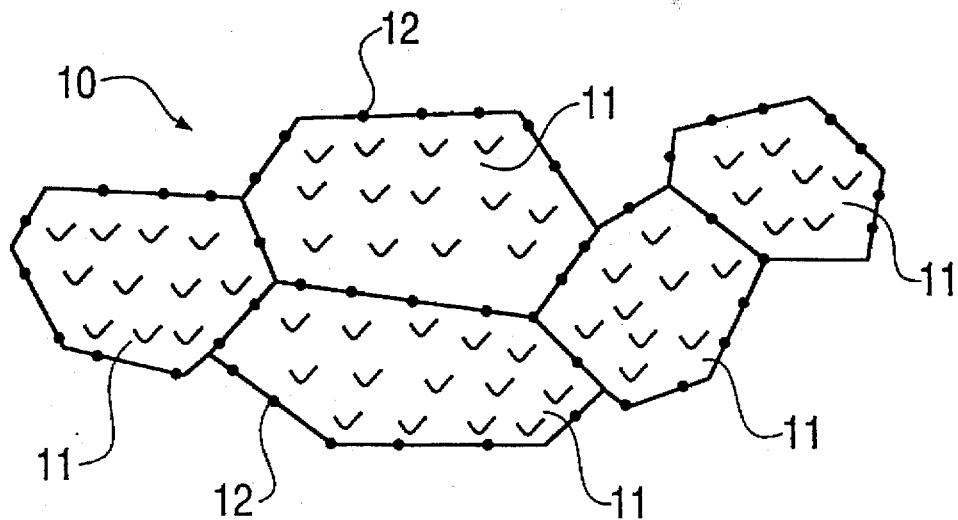
FIG. 1 illustrates the microstructure of a prior art solid electrolyte-ceramic known from U.S. Pat. No. 5,130,210 to Iwasaki et al.

With reference to FIG. 1, as described in U.S. Pat. No. 5,130,210 to Iwasaki et al., a ceramic 10 of a solid electrolytic material contains fully stabilized zirconium dioxide grains 11 with a grain size of between 3 and 20 µm. Metal oxide particles 12 are added to the surface and between the solid electrolyte grains 11 and consist of, for example, aluminum oxide. Metal oxide particles 12 have a substantially smaller grain diameter than the zirconium dioxide grains 11, namely, <1 µm. A complete surrounding of the surface of the zirconium dioxide grains 11 with metal oxide particles 12 is not provided and also not desired, since the electrical or ionic conductivity of the zirconium dioxide grains 11 would be destroyed. The metal oxide particles 12 act as a grain growth inhibitor with which the grain growth of the zirconium dioxide powder is limited during the sintering of the ceramic. Thereby, a mechanically stable ceramic 10 is maintained.

Figure 2:
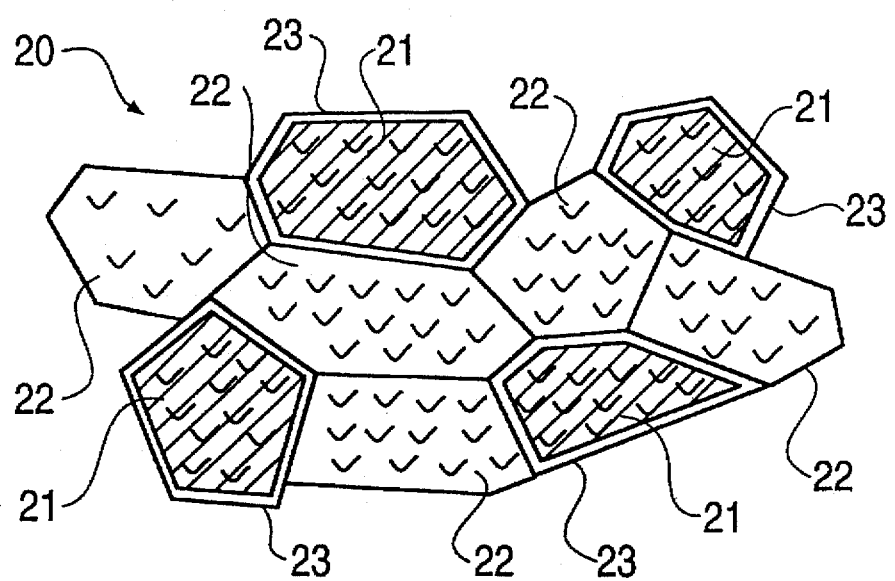
FIG. 2 illustrates the microstructure of a solid electrolyte-ceramic according to the present invention.

A solid electrolyte-ceramic 20, which has a high thermal shock resistance at simultaneously high ionic conductivity according to the present invention, arises from FIG. 2. FIG. 2 illustrates the microstructure of a solid electrolyte-ceramic according to the present invention. The ceramic 20 contains partially stabilized solid electrolyte grains 21 and fully stabilized solid electrolyte grains 22. The grain size of the solid electrolyte grains 21, 22 of the ceramic 20 is smaller in the example of this embodiment than the grain sizes of the solid electrolyte grains 11 of the ceramic 10 according to the prior art illustrated in FIG. 1. The surface of the partially stabilized solid electrolyte grain 21 is provided with a metal oxide layer 23. In the most favorable case, the metal oxide layer 23 surrounds the partially stabilized solid electrolyte grain 21 completely. It is entirely possible, however, that individual partially stabilized solid electrolyte grains 21 are not completely surrounded with the metal oxide layer 23 during creation of the metal oxide layer 23. One strives, however, to encase the partially stabilized solid electrolyte grains 21 as completely as possible by the metal oxide layer. The cross sectional layer thickness of the metal oxide layer 23 measures at most 20%, preferably at most 10%, of the cross sectional particle diameter of the partially stabilized solid electrolyte grain 21.

With the metal oxide layer 23, solid body reactions between the fully stabilized solid electrolyte grains 22 and the partially stabilized solid electrolyte grains 21 are practically eliminated. Thus, the wandering or diffusion of the stabilizing cations from the fully stabilized solid electrolyte region into the region with lower concentration of stabilizers is hindered. As a result, the high ionic conductivity of the fully stabilized solid electrolyte grains 22 remains intact. Since only the partially stabilized solid electrolyte grains 21 are provided with the metal oxide layer 23, the ionic conductivity of the fully stabilized solid electrolyte grains 22 at phase transformation remains intact. Without the addition of the partially stabilized solid electrolyte grains 21, a high ionic conductivity would still be achievable; however, such a solid electrolyte-ceramic does not have sufficient mechanical stability and thermal shock resistance as is necessary, for example, for exhaust gas sensors. The mechanical stability and thermal shock resistance of the ceramic 20 is attained with the partially stabilized solid electrolyte grains 21, in that a matrix stress between the fully stabilized phase and the partially stabilized phase arises.

The production of the powder of the partially stabilized and fully stabilized solid electrolyte grains 21, 22, as well as the incorporation of the metal oxide layer 23 onto the partially stabilized solid electrolyte grains 21, is described in more detail in the following examples.

Embodiments of the invention will now be more particularly described by way of example.

EXAMPLE 1

The aqueous solution of a zirconium salt, for example, $ZrCl_2$, is first combined with the aqueous solution of an yttrium salt, the ratio of the components being set so that the final yttrium oxide-stabilized zirconium dioxide powder has an yttrium oxide content of 9 mol %; the Zr and Y salts are coprecipitated from the combined solutions, calcined and subsequently milled, the average particle size being adjusted to 1.5 µm.

A second ceramic powder based on $ZrO_2$ is prepared by adding a dispersion of aluminum oxide to an aqueous dispersion of zirconium dioxide having a particle size below 0.5 µm, preferably below 0.45 µm, which has been prepared, for example, by reactive decomposition of $ZrCl_2$ in a plasma burner, as described in German Patent 38 13 731, the aluminum oxide content, based on the total of zirconium dioxide and aluminum oxide, being 10% by weight. An aluminum oxide coating is deposited on the zirconium dioxide particles in a known manner, for example, by controlled adjustment of the pH; the product is separated off by filtration, washed and dried.

The two ceramic powders so prepared are then combined in a slip in a weight ratio of the first to the second powder of 90 to 10, spray-dried, optionally with addition of organic binders and/or pressing aids, and subsequently pressed into shaped bodies, or as a casting slip cast into sheets, and sintered at 1400° C. The shaped ceramic bodies thus obtained have improved thermal-shock resistance.

EXAMPLE 2

Initially a first ceramic powder is prepared by coating zirconium dioxide with yttrium oxide. For this purpose, an aqueous dispersion of zirconium dioxide having a particle size in the range from 0.5 µm to 2 µm is combined with an yttrium salt solution, the ratio of the components being set so that the yttrium oxide content, based on the total of yttrium oxide and zirconium dioxide, is 5 mol %. The yttrium hydroxide is precipitated onto the zirconium dioxide particles by controlled adjustment of the pH of the solution; the product is separated off by filtration, washed, dried and calcined.

A second powder is prepared in the manner described in Example 1 by coating zirconium dioxide with aluminum oxide, the aluminum oxide content being set to 10% by weight.

The two powders are then mixed in a slip in a weight ratio of 80:20 of first to second powder, spray-dried, optionally with addition of binders and/or pressing aids, pressed into shaped bodies and sintered at 1400° C. The shaped ceramic bodies thus obtained have increased thermal-shock resistance.

EXAMPLE 3

A first ceramic powder is prepared by melting zirconium dioxide and 9 mol % of yttrium oxide in an electric arc and is milled to a particle size in the range from 1 to 2 µm.

The preparation of the second ceramic powder and the further processing of the first and second ceramic powders is carried out as described in Example 1.

What is claimed is:

1. A ceramic which is thermal shock resistant and which is a sintered, homogeneous mixture of first and second ceramic powders, comprising:
    a first ceramic powder which is comprised of at least one tetravalent oxide selected from the group consisting of zirconium dioxide, hafnium dioxide, and thorium dioxide, and at least one stabilizer oxide selected from the group consisting of oxides effective to stabilize the at least one tetravalent oxide and thereby provide a stabilized oxide after sintering; and
    a second ceramic powder which is comprised of at least one tetravalent oxide selected from the group consisting of zirconium dioxide, hafnium dioxide, and thorium dioxide, and from 0 to 2.5 mole % of at least one stabilizer oxide, and which is at least partly covered by a coating comprised of an oxide material present in an amount (a) which is effective to inhibit diffusion of cations from the at least one stabilizer oxide of the first ceramic powder into the second ceramic powder and (b) which is effective to inhibit uncontrolled grain growth,
    wherein the first ceramic powder has a higher stabilizer oxide content than that of the second ceramic powder, wherein only the second ceramic powder is covered by said coating, and wherein the coating on the grains of the second granular ceramic material comprises at least one oxide material selected from the group consisting of $Al_2O_3$, $Ga_2O_3$, and Na-$\beta$-$Al_2O_3$.

2. The ceramic as defined in claim 1, wherein the second ceramic powder comprises at least on one stabilizer oxide, and wherein the at least one stabilizer oxide of the second ceramic powder includes $Y_2O_3$.

3. The ceramic as defined in claim 1, wherein the first ceramic powder has a content of the at least one stabilizer oxide of at least 4 mole %.

4. The ceramic according to claim 1, wherein the first ceramic powder has a grain size which ranges from 0.5 to 2 µm, and wherein the second ceramic powder has a grain size which is less than 0.5 µm.

5. The ceramic according to claim 1, wherein the first ceramic powder is prepared by coprecipitation of a suspension containing the at least one tetravalent oxide and the at least one stabilizer oxide to provide a coprecipitate, calcination of the coprecipitate, and subsequent milling.

6. The ceramic according to claim 1, wherein the first ceramic powder and the second ceramic powder are present in a weight ratio which ranges from 75:25 to 95:5.

7. The ceramic according to claim 6, wherein the first ceramic powder and the second ceramic powder are present in a weight ratio which ranges from 90:10.

8. The ceramic according to claim 1, wherein the at least one tetravalent oxide of the second ceramic powder comprises a mixture of $ZrO_2$, and wherein the oxide material is $Al_2O_3$.

9. The ceramic according to claim 8, wherein the second ceramic powder comprises 10% by weight of $Al_2O_3$.

10. The ceramic according to claim 1, wherein the first ceramic powder comprises $ZrO_2$, and wherein the at least one stabilizer oxide comprises content ranges from 4 to 10 mole % of $Y_2O_3$.

11. The ceramic according to claim 1, wherein the first ceramic powder is prepared by melting a mixture containing the at least one tetravalent oxide and the at least one stabilizer oxide in an electric arc to provide a melt, cooling the melt to provide a mass, and milling the mass to provide grains having a grain size which ranges from 1 to 2 µm.

12. The ceramic according to claim 1, wherein the ceramic is a ceramic solid electrolyte suitable for use in a gas sensor.

13. A ceramic which is thermal shock resistant, which has a good oxygen ion conductivity effective for use of the ceramic in a measuring sensor of exhaust gases, and which is a sintered, homogeneous mixture of first and second ceramic powders, comprising:
    a first granular ceramic material which is comprised of at least one tetravalent oxide selected from the group consisting of zirconium dioxide, hafnium dioxide, and thorium dioxide, and at least one stabilizer oxide selected from the group consisting of oxides effective to stabilize the at least one tetravalent oxide and thereby provide a fully stabilized oxide having good oxygen ion conductivity; and
    a second granular ceramic material which is comprised of at least one tetravalent oxide selected from the group consisting of zirconium dioxide, hafnium dioxide, and thorium dioxide, and at least one stabilizer oxide in an amount which ranges up to 2.5 mole %, and in which the grains thereof are substantially covered by a coating comprised of an oxide material present in an amount (a) which is effective to inhibit diffusion of cations from the at least one stabilizer oxide in the first ceramic powder into the second ceramic powder and (b) which is effective to inhibit uncontrolled grain growth,
    wherein the first ceramic powder has a higher stabilizer oxide content than that of the second ceramic powder, wherein only the second granular ceramic material is covered by said coating, and wherein the coating on the grains of the second granular ceramic material comprises at least one oxide material selected from the group consisting of $Al_2O_3$, $Ga_2O_3$, and Na-$\beta$-$Al_2O_3$.

14. The ceramic according to claim 13, wherein the first granular ceramic material has a grain size which ranges from 0.5 to 2 µm, and wherein the second granular ceramic material has a grain size which is less than 0.5 µm.

15. The ceramic according to claim 13, wherein the first granular ceramic material and the second granular ceramic material are present in a weight ratio which ranges from 75:25 to 95:5.

16. The ceramic according to claim 13, wherein the first granular ceramic material and the second granular ceramic material comprise $ZrO_2$, wherein the at least one stabilizer oxide contained in the first granular ceramic material and in the second granular ceramic material is $Y_2O_3$, and wherein the $Y_2O_3$ in the first granular ceramic material is present in an amount ranging from 4 to 10 mole %.

* * * * *